United States Patent
Liu et al.

(12) 
(10) Patent No.: US 6,479,150 B1
(45) Date of Patent: Nov. 12, 2002

(54) LAYER MATERIALS TREATED WITH SURFACTANT-MODIFIED HYDROPHOBIC ODOR CONTROL AGENTS

(75) Inventors: Yuelong Liu, Alpharetta, GA (US); Roger Bradshaw Quincy, III, Cumming, GA (US); Garry Roland Woltman, Greenville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/472,934

(22) Filed: Dec. 28, 1999

Related U.S. Application Data

(60) Provisional application No. 60/121,737, filed on Feb. 26, 1999.

(51) Int. Cl.[7] .............................. B32B 27/04; B32B 9/04
(52) U.S. Cl. ..................................... 428/411.1; 442/121
(58) Field of Search .......................... 428/305.5, 411.1, 428/423.5, 424.2, 424.4, 424.8; 442/121

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,485,706 A | 12/1969 | Evans | 161/72 |
| 3,502,538 A | 3/1970 | Petersen | 161/150 |
| 3,502,763 A | 3/1970 | Hartmann | 264/210 |
| 3,534,075 A | 10/1970 | Andress, Jr. | 260/404.5 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,855,046 A | 12/1974 | Hansen et al. | 161/150 |
| 3,901,236 A | 8/1975 | Assarsson et al. | 128/284 |
| 3,903,259 A | 9/1975 | Hart | 424/76 |
| 3,920,020 A | 11/1975 | Kraskin | 128/290 |
| 4,015,050 A | 3/1977 | Birchall et al. | 428/480 |
| 4,076,663 A | 2/1978 | Masuda et al. | 260/17.4 GC |
| 4,100,324 A | 7/1978 | Anderson et al. | 428/288 |
| 4,273,786 A | 6/1981 | Kraskin | 424/319 |
| 4,286,082 A | 8/1981 | Tsubakimoto et al. | 526/240 |
| 4,300,561 A | 11/1981 | Kaczmarzyk et al. | 128/285 |
| 4,340,563 A | 7/1982 | Appel et al. | 264/518 |
| 4,356,190 A | 10/1982 | Kraskin | 424/319 |
| 4,377,167 A | 3/1983 | Kaczmarzyk et al. | 128/285 |
| 4,425,130 A | 1/1984 | Des Marais | 604/389 |
| 4,617,230 A | 10/1986 | Shah et al. | 428/288 |
| 4,638,058 A | 1/1987 | Brandt et al. | 536/103 |
| 4,818,464 A | 4/1989 | Lau | 264/510 |
| 4,929,378 A | 5/1990 | Morita et al. | 252/105 |
| 5,108,820 A | 4/1992 | Kaneko et al. | 428/198 |
| 5,161,686 A | 11/1992 | Weber et al. | 206/440 |
| 5,336,552 A | 8/1994 | Strack et al. | 428/224 |
| 5,348,667 A | 9/1994 | Bacon et al. | 252/8.6 |
| 5,382,400 A | 1/1995 | Pike et al. | 264/168 |
| 5,429,628 A | 7/1995 | Trinh et al. | 604/359 |
| 5,445,747 A | 8/1995 | Kvietok et al. | 252/86 |
| 5,533,990 A | 7/1996 | Yeo | 604/363 |
| 5,534,165 A | 7/1996 | Pilosof et al. | 252/8.91 |
| 5,571,782 A | 11/1996 | Trinh et al. | 512/4 |
| 5,578,563 A | 11/1996 | Trinh et al. | 510/513 |
| 5,591,146 A | 1/1997 | Hasse | 604/359 |
| 5,593,670 A | 1/1997 | Trinh et al. | 424/76.1 |
| 5,594,125 A | 1/1997 | Seyschab et al. | 536/103 |
| 5,648,067 A | 7/1997 | Dillenburg et al. | 424/65 |
| 5,663,134 A | 9/1997 | Trinh et al. | 510/406 |
| 5,668,097 A | 9/1997 | Trinh et al. | 510/293 |

(List continued on next page.)

FOREIGN PATENT DOCUMENTS

| | | | |
|---|---|---|---|
| EP | 392 607 | 10/1990 | |
| EP | 392 608 | 10/1990 | |
| EP | 510 619 | 10/1992 | |
| EP | 0 562 620 A1 | 9/1993 | |
| EP | 562 620 | 9/1993 | |
| EP | 685 213 | 12/1995 | |
| EP | 0 894 502 A1 | 7/1997 | ........... A61L/15/18 |
| EP | 811 390 | 12/1997 | |
| EP | 811 391 | 12/1997 | |
| EP | 813 848 | 12/1997 | |
| GB | 1 517 042 | 5/1975 | |
| WO | 94 22500 | 10/1994 | |
| WO | WO 95/17175 | 6/1995 | ........... A61K/9/70 |
| WO | 96 04937 | 2/1996 | |
| WO | 96 05358 | 2/1996 | |
| WO | 96/24318 | 8/1996 | |
| WO | 97/31698 | 9/1997 | ........... B01D/53/04 |
| WO | 98 07455 | 2/1998 | |
| WO | 98 17239 | 4/1998 | |
| WO | 98 17240 | 4/1998 | |
| WO | 98 18439 | 5/1998 | |
| WO | 98/20916 | 5/1998 | ........... A61L/15/46 |
| WO | 98 26808 | 6/1998 | |
| WO | WO 98/56342 | 12/1998 | ........... A61K/7/48 |
| WO | 99/45973 | 9/1999 | |
| WO | 99/45974 | 9/1999 | |
| WO | 00/10500 | 3/2000 | |

OTHER PUBLICATIONS

Dharmawardana, Udeni R., et al.: *A Surface Tension Method for Determining Binding Constants for Cyclodextrin Inclusion Complexes of Ionic Surfactants*, Langmuir, vol. 9, No. 9, 2258–2263, 1993.

U. Denter et al.: *Verfahrenstechnische Methoden zur permanenten Fixierung von Cyclodextrindervaten auf textilen Oberflächen*, Textilveredlung, 33–39, vol. 32, No. 1/2, 1997.

*Primary Examiner*—John Hardee
(74) *Attorney, Agent, or Firm*—Pauley Petersen Kinne & Erickson

(57) ABSTRACT

A treated layer material has at least one hydrophilic, odor-absorbing surface which is wettable to aqueous liquids and capable of controlling a wide variety of malodors. The layer material is treated with a hydrophilic surfactant-modified odor control agent prepared by mixing or chemically reacting a hydrophobic odor control agent with a surfactant or surfactant-producing compound. The layer material thus treated can be used in a wide variety of personal care and medical absorbent products, as well as other applications.

33 Claims, No Drawings

U.S. PATENT DOCUMENTS

| | | | | |
|---|---|---|---|---|
| 5,670,475 A | | 9/1997 | Trinh et al. | 510/470 |
| 5,685,872 A | | 11/1997 | Syverson | 604/360 |
| 5,690,919 A | | 11/1997 | Röckl et al. | 424/65 |
| 5,698,476 A | | 12/1997 | Johnson et al. | 442/121 |
| 5,714,137 A | | 2/1998 | Trinh et al. | 424/76.4 |
| 5,714,445 A | | 2/1998 | Trinh et al. | 510/103 |
| 5,718,887 A | | 2/1998 | Wolf et al. | 424/65 |
| 5,733,272 A | | 3/1998 | Brunner et al. | 604/359 |
| 5,738,860 A | * | 4/1998 | Schonfeldt et al. | 424/402 |
| H1732 H | | 6/1998 | Johnson | 428/68 |
| 5,769,833 A | | 6/1998 | Hasse | 604/359 |
| 5,780,020 A | | 7/1998 | Peterson et al. | 424/65 |
| 5,785,697 A | | 7/1998 | Trombetta et al. | 604/378 |
| 5,821,215 A | | 10/1998 | Crudden et al. | 510/392 |
| 5,849,325 A | * | 12/1998 | Heinecke et al. | 424/443 |
| 5,860,959 A | * | 1/1999 | Gent | 604/332 |
| 5,865,792 A | | 2/1999 | Ledger et al. | 604/20 |
| 5,871,718 A | | 2/1999 | Lucas et al. | 424/65 |
| 5,871,719 A | | 2/1999 | Lucas et al. | 424/65 |
| 5,874,067 A | * | 2/1999 | Lucas et al. | 424/65 |
| 5,928,631 A | | 7/1999 | Lucas et al. | 424/65 |
| 5,932,495 A | | 8/1999 | Boney et al. | 442/121 |
| 5,942,217 A | | 8/1999 | Woo et al. | 424/76.1 |
| 5,955,093 A | | 9/1999 | Woo et al. | 424/401 |
| 5,968,404 A | | 10/1999 | Trinh et al. | 252/8.91 |
| 5,997,759 A | | 12/1999 | Trinh et al. | 252/8.91 |
| 6,001,343 A | | 12/1999 | Trinh et al. | 424/76.4 |
| 6,021,822 A | * | 2/2000 | Izawa et al. | 141/110 |
| 6,028,016 A | | 2/2000 | Yahiaoui et al. | 442/118 |
| 6,031,147 A | | 2/2000 | Gross | 604/359 |
| 6,033,486 A | | 3/2000 | Andros | 134/6 |
| 6,033,679 A | | 3/2000 | Woo et al. | 424/401 |
| 6,066,673 A | | 5/2000 | McIver et al. | 514/634 |
| 6,100,233 A | | 8/2000 | Sivik et al. | 512/26 |
| 6,106,738 A | | 8/2000 | Woo et al. | 252/8.91 |
| 6,229,062 B1 | | 5/2001 | Mandell et al. | 604/367 |
| 6,296,936 B1 | | 10/2001 | Yahiaoui et al. | 428/378 |

* cited by examiner

LAYER MATERIALS TREATED WITH SURFACTANT-MODIFIED HYDROPHOBIC ODOR CONTROL AGENTS

This application claims benefit of Provisional Application No. 60/121,737, filed Feb. 26, 1999.

FIELD OF THE INVENTION

This invention relates to chemical compounds and blends which prevent or control odor and impart surface wetting properties to layer materials. In particular, the invention relates to layer materials treated with these dual purpose chemical compounds and blends.

BACKGROUND OF THE INVENTION

Nonwoven fabrics, films, foams, and other layer materials and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. Films, foams, and other layer materials are also employed in some of these applications, and may be combined with nonwoven webs.

It is not always possible to efficiently produce a layer material having all the desired properties as formed, and it is frequently necessary to treat the material with a surfactant to improve or alter surface properties such as wettability by one or more fluids, repellency to one or more fluids, electrostatic characteristics, conductivity, and softness, to name just a few examples. Conventional surface treatments involve steps such as dipping the substrate in a treatment bath, coating or spraying the substrate with the treatment composition, and printing the substrate with the treatment composition. For cost and other reasons it is usually desired to use the minimum amount of treatment composition that will produce the desired effect with an acceptable degree of uniformity.

For many thermoplastic layer material end use applications, it is desirable to reduce, prevent, or eliminate odors. For diapers and other incontinence products, it is desirable to reduce or eliminate the odor of ammonia which is formed from urine. For feminine hygiene products, it is desirable to reduce or eliminate the odor of triethylamine. Other common odor-producing substances include isovaleric acid, dimethyl disulfide, and dimethyl trisulfide.

Odor control agents include odor inhibitors, odor absorbers, odor adsorbers, and other compounds which reduce, prevent, or eliminate odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrin.

Certain odor control agents are hydrophobic, and cannot easily be applied from aqueous solutions to substrates because they do not dissolve or disperse in water. Even if these odor control agents could be applied from solution, they would not easily wet the substrate, or render its surface wettable, due to their hydrophobic nature. Examples of hydrophobic odor control agents include, without limitation, those having aromatic chemistries.

Personal care products such as diapers and feminine care pads typically contain polyolefin nonwoven fabrics. Hydrophobic odor control agents cannot usually be applied to the fabric surfaces of personal care products. These agents are usually introduced as powders or capsules to the product, resulting in several drawbacks. For example, placement and containment of the powders or capsules in the product can be troublesome. More importantly, powders and capsules do not present optimum surface area for odor absorption due to a rather low surface to volume ratio. Therefore, more odor control agent will be needed if in one of these forms.

There is a need or desire for odor-preventing and odor-absorbing compounds and blends which can be applied to a substrate (e.g., a thermoplastic or other hydrophobic substrate) in a liquid or solvent form, and which have enough surface wetting properties to facilitate even fluid distribution and durability.

SUMMARY OF THE INVENTION

The present invention is directed to a surfactant-modified odor control agent formed by either a) blending a hydrophobic odor control agent with a surfactant, or b) chemically reacting a hydrophobic odor control agent with a surfactant-producing compound. Surfactant-producing compounds include surfactants, and other compounds that transform the hydrophobic odor control agents into surfactants following the chemical reaction. The invention is also directed to a layer material which has been treated with the surfactant-modified odor control agent. The surfactant-modified odor control agent can be applied to the layer material using conventional internal or external application techniques, and is preferably applied using an external application technique. The resulting treated substrate is more wettable to aqueous liquids, and prevents, reduces and/or absorbs odors at its surfaces.

The substrate layer material can be a hydrophobic material, and can be a thermoplastic material made using one or more thermoplastic polymers. The layer material can be porous and water-permeable. For instance, the layer material can be a thermoplastic nonwoven filament web, a thermoplastic film, a foam layer, or a combination thereof A thermoplastic nonwoven filament web is preferred. The treated layer material can be used in a wide variety of personal care products and medical products, and in other applications.

The surfactant-modified odor control agents can be applied to hydrophobic or other substrates (for example, polyolefin-based films, foam layers and nonwoven webs) from an aqueous solution, because the surface tension of the solution is low enough to wet out the low surface energy substrate. For instance, the coating of the surfactant-modified odor control agent on the polyolefin fibers of a polyolefin nonwoven fabric will optimize the surface to volume ratio of odor control chemistry, and thus provide better odor control (e.g., odor absorption, adsorption, prevention or inhibition). Furthermore, fibers coated with a surfactant-modified odor control agent will be in direct contact with body fluids as the fluids enter and wick through the fabric components of the personal care product. This will provide optimum odor control since the odors are believed to emanate from the body fluids.

It is thus a feature and advantage of the invention to provide a surfactant-modified odor control agent having the odor control properties of a hydrophobic odor control agent, which can be applied to a substrate using solution techniques.

It is also a feature and advantage of the invention to provide a treated layer material having at least one surface which is more wettable to aqueous liquids then the untreated layer material, and which inhibits and/or absorbs common odors.

It is also a feature and advantage of the invention to provide a personal care fabric or product which utilizes the treated layer material that is more wettable, and inhibits and/or absorbs odors on at least one outer surface.

It is also a feature and advantage of the invention to provide a medical fabric or product which utilizes the treated layer material that is more wettable, and inhibits and/or absorbs odors on at least one outer surface.

DEFINITIONS

The term "layer material" refers to a material that exists in the form of a flexible, fabric-like or paper-like material, including without limitation nonwoven filament webs and fabrics, thermoplastic films, flexible thermoplastic foam materials, and multilayer combinations including one or more of these.

The term "water-permeable porous layer material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

The term "monocomponent" fiber refers to a fiber formed from one or more extruders using only one polymer. This is not meant to exclude fibers formed from one polymer to which small amounts of additives have been added for color, anti-static properties, lubrication, hydrophilicity, repellency, etc. These additives, e.g., titanium dioxide for color, are generally present in an amount less than 5 weight percent and more typically about 2 weight percent or less.

The term "coform material" refers to a product containing about 10–90% by weight of thermoplastic meltblown fibers and about 10–90% by weight of staple-length pulp fibers dispersed within the meltblown fiber matrix. More commonly, coform materials contain about 20–70% by weight thermoplastic meltblown fibers and about 30–80% by weight pulp fibers.

The term "film" refers to a thermoplastic film made using a film extrusion process, such as a cast film or blown film extrusion process. The term "water-permeable porous films" refers to films rendered porous by puncturing or aperturing, and to films rendered porous by mixing polymer with filler, forming a film from the mixture, and stretching the film.

The term "foam material" refers to a thermoplastic layer material made with the aid of a foaming process. The term "open-celled foam material" refers to a foam layer whose cells interconnect, or otherwise create pores from one surface of the layer to the opposite surface.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "bicomponent filaments or fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and U.S. Pat. No. 5,382,400 to Pike et al., each of which is incorporated herein in its entirety by reference. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "average pulp fiber length" refers to a weighted average length of pulp determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k}(X_i*n_i)/n$$

where k=maximum fiber length, $X_i$=individual fiber length, $n_i$=number of fibers having length $X_i$ and n=total number of fibers measured.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "through-air bonding" or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provides the bonding. Through-air bonding has restricted variability and is generally regarded as a second step bonding process. Since TAB requires the melting of at least one component to accomplish bonding, it is restricted to webs with two components such as bicomponent fiber webs or webs containing an adhesive fiber or powder.

The term "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g., like a window screen. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

The term "personal care product" includes without limitation diapers, training pants, swim wear, absorbent underpants, baby wipes, adult incontinence products, and feminine hygiene products.

The term "medical product" includes without limitation garments, underpads, bandages, absorbent drapes, and medical wipes.

The term "hydrophilic" or "wettable" means that the polymeric material has an apparent surface free energy such that the polymeric material is wettable by an aqueous medium, i.e., a liquid medium of which water is a major component. That is, an aqueous medium wets the nonwoven fabric. "Apparent surface free energy" refers to the highest surface tension of an aqueous liquid which wets the polymeric material. For example, the apparent surface free energy of a polymeric material that is wetted by an aqueous liquid having a surface tension of 72 dynes/cm, is at least 72 dynes/cm and possibly higher. In the fabrics of the invention, a surface of the nonwoven fabric has been treated with a surfactant-modified odor control agent using internal or external application techniques as described below.

The term "surfactant" refers to a compound or blend which, when applied to a surface of a substrate, causes the surface to become more "wettable" as defined above. In one instance, the substrate is not independently wettable and the surfactant causes it to become wettable. In another instance, the substrate is somewhat wettable and the surfactant causes it to become more wettable, or more easily wetted.

The term "surfactant-producing moiety" or "surfactant-producing compound" refers to a chemical group or compound which, when reacted or blended with another compound (e.g., an odor control agent) causes the reacted compound or blend to behave as a surfactant. The surfactant-producing moiety or compound may or may not behave as a surfactant prior to the chemical reaction or blending.

The term "odor control agent" includes compounds and blends which inhibit the formation of at least one undesirable odor, as well as compounds and blends which absorb an undesirable odor that has already formed.

The term "surfactant-modified odor control agent" refers to a blend, and/or a reaction product, between an odor control agent and a surfactant or surfactant-producing moiety, which acts as both a surfactant and an odor control agent.

DETAILED DESCRIPTION OF THE PRESENTLY PREFERRED EMBODIMENTS

The present invention is directed to a surfactant-modified odor control agent, a layer material treated with the surfactant-modified odor control agent, and an absorbent product which utilizes the treated layer material. The surfactant-modified odor control agent is prepared by a) blending a hydrophobic odor control agent with a surfactant, and/or b) chemically reacting a hydrophobic odor control agent with a surfactant-producing compound. The term surfactant-producing compound" includes surfactants, and other hydrophilic compounds which transform the hydrophobic odor-control agents into surfactants following the chemical reaction. The blending and/or chemical reaction can be accomplished using techniques familiar to persons skilled in the art.

Hydrophobic odor control agents include any odor control agent which is antagonistic to water, and incapable of dissolving in water. Suitable hydrophobic odor control agents include aromatic odor control agents. Examples include phenolic derivatives having antimicrobial effects which inhibit the growth of odor-producing bacteria. Cresols, and diphenyl compounds such as hexachlorophene, are among this group of odor inhibitors. Other aromatic odor control agents include without limitation alkyl-modified aromatic compounds, for example, alkyl-modified cyclophanes and derivatives thereof. Preferred alkyl groups attached to the aromatic ring have from about 3 to about 18 carbon atoms. Other hydrophobic odor control agents include hydrophobic compounds which reduce, inhibit, prevent, or otherwise control undesirable odors from common sources such as ammonia, triethylamine, isovaleric acid, dimethyl disulfide, dimethyl trisulfide, indole, skatole, and the like.

Hydrophilic surfactants, and surfactant-producing compounds, include surfactants and other compounds with functional groups having an affinity for water, wettable by water, and/or having a tendency to render other materials and compounds wettable by water. Examples of surfactants or surfactant-producing compounds which may either be blended or chemically attached to a hydrophobic odor control agent include, without limitation, polyethylene glycols, polyethylene glycol-polypropylene glycol block copolymers, polyolefin glycol methyl ethers (for example, polyethylene glycol methyl ethers), polyvinyl alcohols, polyacrylic acids, polyvinyl pyrrolidones, and derivatives and combinations thereof. Other compounds having hydroxyl, carboxyl, amino, or amido groups may also be useful. Preferred hydrophilic surfactants are polyolefin glycols and polyolefin glycol methyl ethers having a weight average molecular weight of about 600–20,000, more preferably about 1000–9000.

The hydrophobic odor control agents and hydrophilic surfactant-producing compounds can be blended or chemically reacted using techniques familiar to persons skilled in the art of organic chemistry. For example, an alkylated phenol may be attached to a polyethylene glycol, polyacrylic acid or other carboxyl compound to yield a surfactant-modified odor control agent having the following general formula:

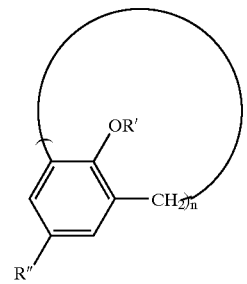

Where one of R' and R" is a polyethylene glycol, polyacrylic acid, or another hydrophilic functional (e.g., sulfonic, hydroxyl, carboxyl, amino or amido) compound, the other of R' and R" is an alkyl group having 3 to 18 carbon atoms, and n is an integer from 3 to 8.

Surfactant-modified odor control agents having this general formula can be collectively referred to as Calix (n) arenes.

The starting layer material is treated with the surfactant-modified odor control agent. The surfactant-modified odor control agent is applied to the layer material using conventional techniques for applying surfactants internally or externally. Preferably, the surfactant-modified odor control agent is applied externally in the form of a liquid, using techniques such as dipping, spraying, brushing, or other liquid coating techniques. The surfactant-modified odor control agent may be blended with water or another solvent to facilitate its application.

Examples of suitable layer materials include without limitation thermoplastic layer materials, for example, thermoplastic nonwoven filament webs, thermoplastic films, and thermoplastic foam layers. The layer material can be a porous, water-permeable layer material. Examples of water-permeable layer materials include thermoplastic nonwoven filament webs, open-celled foam layers, and films which are apertured or otherwise rendered porous, such as by stretching a film made from a mixture of a thermoplastic material and a particulate filler.

The preferred layer material used in the invention is a nonwoven web including a plurality of filaments made from one or more polymers. The nonwoven web may be a spunbond web, a meltblown web, a bonded carded web, or another type of nonwoven web, and may be present in a single layer or a multilayer composite including one or more nonwoven web layers, and in some instances, one or more film or foam layers. The web may include monocomponent or bicomponent filaments, or a combination including one or both filament types. The nonwoven web may have a variety of basis weights, preferably ranging from about 0.1–200 grams per square meter (gsm). One preferred nonwoven web is a coform material, which includes a matrix of polyolefin meltblown fibers and a large percentage (often 30–80% by weight) of pulp fibers dispersed in the matrix of meltblown fibers. Another preferred nonwoven web is an airlaid web of polyolefin fibers and pulp fibers.

A wide variety of thermoplastic polymers may be used to construct the starting layer material, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing. Polyolefins are preferred. Polyethylene and polypropylene homopolymers and copolymers are most preferred.

The surfactant-modified odor control agent may be applied using internal or external application techniques known in the art. Some compounds and blends operate more favorably when applied internally and are called "internal additives." Others operate more favorably when applied externally and are called "external additives." Still other compounds and blends operate suitably as both internal and external additives.

As is generally known, an internal additive is typically blended with the polymer used to make the nonwoven web, film, foam, or other layer material, and migrates to the surfaces of the nonwoven web filaments or other layer material during and/or after their formation. Often, the migration results from a stimulus, such as heat applied to the layer material. An external additive is applied externally to the surfaces of the layer material after it is formed. An external additive may be applied by dipping, soaking, spraying, or otherwise coating the layer material with a solvent or other medium containing the additive.

External application methods are presently preferred for the surfactant-modified odor control agents used with the treated materials of the invention. The surfactant-modified odor control agent (whether formed by blending or chemical reaction) may be mixed with water or another suitable solvent in a concentration of about 0.1–30% by weight of the agent, preferably about 0.5–15% by weight of the agent, more preferably about 1–5% by weight of the agent. The solution may then be applied to a layer material or web by immersion, spraying, brush coating, printing, or another suitable technique. The treated layer material can then be dried using heat, forced air convection, vacuum-induced evaporation, or another conventional drying technique.

The treated layer materials thus formed have wettability to aqueous liquids, and odor resistance to a wide variety of odor-producing moieties. The terms "odor resistance" and "odor control" refer to the ability of the treated layer materials to react with, inhibit, neutralize, form complexes with, or otherwise prevent the odor-producing compounds from forming, or reduce the odors produced by them. Examples of odor-producing compounds which the fabrics of the invention may inhibit, reduce or eliminate, include without limitation ammonia, triethylamine, isovaleric acid, dimethyldisulfide, dimethyltrisulfide, indole, skatole, and the like.

The amount of surfactant-modified odor control agent needed to provide sufficient wetting and odor absorption may vary depending on the surfactant moiety and odor control agent blended or reacted together, the base polymer type, and whether the surfactant-modified odor control agent is added internally or externally. On a solvent-free weight basis, the surfactant-modified odor control agent should generally constitute about 0.05–10% by weight of the layer material to which it is applied, preferably about 0.1–5% by weight, more preferably about 1–3% by weight.

The treated layer materials thus formed can be used in a wide variety of absorbent product applications including, in particular, personal care absorbent products. Personal care absorbent products include diapers, training pants, swim wear, absorbent underpants, baby wipes, adult incontinence products, feminine hygiene products, and the like. In absorbent products, the treated layer material (if water permeable) can be used as a cover sheet or containment matrix for an absorbent medium capable of absorbing aqueous liquids. An absorbent medium may include, for instance, pulp fibers alone or in combination with a superabsorbent material. The treated layer material can also be used in medical absorbent products, including without limitation garments, underpads, absorbent drapes, bandages, and medical wipes.

The pulp fibers may be any high-average fiber length pulp, low-average fiber length pulp, or mixtures of the same. Preferred pulp fibers include cellulose fibers. The term "high average fiber length pulp" refers to pulp that contains a relatively small amount of short fibers and non-fiber particles. High fiber length pulps typically have an average fiber length greater than about 1.5 mm, preferably about 1.5–6 mm, as determined by an optical fiber analyzer, such as the Kajaani tester referenced above. Sources generally include non-secondary (virgin) fibers as well as secondary fiber pulp which has been screened. Examples of high average fiber length pulps include bleached and unbleached virgin softwood fiber pulps.

The term "low average fiber length pulp" refers to pulp that contains a significant amount of short fibers and non-fiber particles. Low average fiber length pulps have an average fiber length less than about 1.5 mm, preferably about 0.7–1.2 mm, as determined by an optical fiber analyzer such as the Kajaani tester referenced above. Examples of low fiber length pulps include virgin hardwood pulp, as well as secondary fiber pulp from sources such as office waste, newsprint, and paperboard scrap.

Examples of high average fiber length wood pulps include those available from the U.S. Alliance Coosa Pines Corporation under the trade designations Longlac 19, Coosa River 56, and Coosa River 57. The low average fiber length pulps may include certain virgin hardwood pulp and secondary (i.e., recycled) fiber pulp from sources including newsprint, reclaimed paperboard, and office waste. Mixtures of high average fiber length and low average fiber length pulps may contain a predominance of low average fiber length pulps. For example, mixtures may contain more than about 50% by weight low-average fiber length pulp and less than about 50% by weight high-average fiber length pulp.

The term "superabsorbent" or "superabsorbent material" refers to a water swellable, water-insoluble organic or inorganic material capable, under the most favorable conditions, of absorbing at least about 20 times its weight and, more desirably, at least about 30 times its weight in an aqueous solution containing 0.9 weight percent sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semispiral, cubic, rod-like, polyhedral, etc. Needles, flakes, fibers, and combinations may also be used.

Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® SXM880, available from Stockhausen, located in Greensboro, N.C. An example of a fibrous superabsorbent is OASIS® 101, available from Technical Absorbents, located in Grimsby, United Kingdom.

As indicated above, the treated layer material may be a cover sheet or a matrix for an absorbent medium. Nonwoven filaments may be employed as a matrix, and may be combined with pulp fibers and (optionally) a superabsorbent material using processes well known in the art. For example, a coform process may be employed, in which at least one meltblown diehead is arranged near a chute through which other materials are added while the web is forming. Coform processes are described in U.S. Pat. No. 4,818,464 to Lau and U.S. Pat. No. 4,100,324 to Anderson et al., the disclosures of which are incorporated by reference. Thermoplastic nonwoven filaments and pulp fibers may also be combined using hydraulic entangling or mechanical entangling. A hydraulic entangling process is described in U.S. Pat. No. 3,485,706 to Evans, the disclosure of which is incorporated by reference.

When treated thermoplastic nonwoven filaments are used as a matrix for an absorbent nonwoven web composite, the composite should contain about 5–97% by weight pulp fibers, preferably about 35–95% by weight pulp fibers, more preferably about 50–95% by weight pulp fibers. When a superabsorbent material is present, it should constitute about 5–90% by weight of the composite, preferably about 10–60% by weight, more preferably about 20–50% by weight. In either case, the thermoplastic nonwoven filament matrix should constitute about 3–95% by weight of the composite, preferably about 5–65% by weight, more preferably about 5–50% by weight.

After combining the ingredients together, the absorbent nonwoven composites may be bonded together using the thermal point bonding or through-air bonding techniques described above, to provide a coherent high integrity structure.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A treated thermoplastic layer mater comprising a substrate layer treated with a surfactant-modified odor control agent produced by chemically attaching one of a surfactant and a surfactant-producing compound to a hydrophobic odor control agent, wherein the surfactant or surfactant-producing compound comprises a polyolefin glycol compound.

2. The treated layer material of claim 1, wherein the substrate layer comprises a thermoplastic nonwoven filament web.

3. The treated layer material of claim 1, wherein the substrate layer comprises a thermoplastic film.

4. The treated layer material of claim 1, wherein the substrate layer comprises a thermoplastic foam layer.

5. The treated layer material of claim 1, wherein the substrate layer comprises a water-permeable layer.

6. The treated layer material of claim 1, wherein the hydrophobic odor control agent comprises an aromatic odor control agent.

7. The treated layer material of claim 6, wherein the aromatic odor control agent comprises a phenolic compound.

8. The treated layer material of claim 6, wherein the aromatic odor control agent comprises an alkyl-modified aromatic compound.

9. The treated layer material of claim 8, wherein the alkyl-modified aromatic compound comprises an alkyl-modified cyclophane or derivative thereof.

10. The treated layer material of claim 8, wherein the alkyl-modified aromatic compound comprises an alkyl group having about 3–18 carbon atoms.

11. The treated layer material of claim 1, wherein the polyolefin glycol compound comprises polyethylene glycol.

12. The treated layer material of claim 1, wherein the polyolefin glycol compound comprises polypropylene glycol.

13. The treated layer material of claim 1, wherein the polyolefin glycol compound comprises a polyethylene glycol-polypropylene glycol combination.

14. The treated layer material of claim 1, wherein the polyolefin glycol compound comprises a polyolefin glycol methyl ether.

15. The treated layer material of claim 1, comprising about 0.05–10% by weight of the surfactant-modified odor control agent.

16. The treated layer material of claim 1, comprising about 0.1–5% by weight of the surfactant-modified odor control agent.

17. The treated layer material of claim 1, comprising about 1–3% by weight of the surfactant-modified odor control agent.

18. The treated layer material of claim 1, wherein the substrate layer comprises a polymer selected from the group consisting of polyamides, polyolefins, polyesters, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing.

19. The treated layer material of claim 1, wherein the substrate layer comprises a polyolefin.

20. The treated layer material of claim 1, wherein the substrate layer comprises a polyethylene homopolymer or copolymer.

21. The treated layer material of claim 1, wherein the substrate layer comprises a polypropylene homopolymer or copolymer.

22. A treated layer material comprising a substrate layer treated with a surfactant-modified odor control agent selected from the group consisting of a) a blend of a surfactant with a hydrophobic odor control agent, b) a reaction product of a surfactant-producing compound with a hydrophobic odor control agent, and c) combinations of the foregoing;
wherein the surfactant-modified odor control agent comprises a compound having the following general formula:

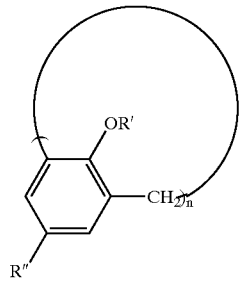

Where one of R' and R" is selected from polyethylene glycols, polyacrylic acids, and other hydroxyl functional, carboxyl functional, sulfonic, amino and amido compounds, the other of R' and R" is selected from alkyl groups having 3 to 18 carbon atoms, and
n is an integer from 3 to 8.

23. The treated layer material of claim 22, comprising about 0.05–10% by weight of the surfactant-modified odor control agent.

24. The treated layer material of claim 22, comprising about 0.1–5% by weight of the surfactant-modified odor control agent.

25. The treated layer material of claim 22, comprising about 1–3% by weight of the surfactant-modified odor control agent.

26. The treated layer material of claim 22, wherein the substrate layer comprises a polymer selected from the group consisting of polyamides, polyolefins, polyesters, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing.

27. The treated layer material of claim 22, wherein the substrate layer comprises a polyolefin.

28. The treated layer material of claim 22, wherein the substrate layer comprises a polyethylene homopolymer or copolymer.

29. The treated layer material of claim 22, wherein the substrate layer comprises a polypropylene homopolymer or copolymer.

30. The treated layer material of claim 22, wherein the substrate layer comprises a thermoplastic nonwoven filament web.

31. The treated layer material of claim 22, wherein the substrate layer comprises a thermoplastic film.

32. The treated layer material of claim 22, wherein the substrate layer comprises a thermoplastic foam layer.

33. The treated layer material of claim 22, wherein the substrate layer comprises a water-permeable layer.

* * * * *